United States Patent [19]

Reese et al.

[11] Patent Number: 5,553,608
[45] Date of Patent: Sep. 10, 1996

[54] FACE MASK WITH ENHANCED SEAL AND METHOD

[75] Inventors: George D. Reese, Arlington; Albert R. Rich, Jr., Watauga; Kevin K. Brunson, Argyle, all of Tex.

[73] Assignee: Tecnol Medical Products, Inc., Fort Worth, Tex.

[21] Appl. No.: 278,930

[22] Filed: Jul. 20, 1994

[51] Int. Cl.⁶ .............................. A62B 18/08; A62B 7/10; A62B 23/02; A62B 18/02
[52] U.S. Cl. .................. 128/206.24; 128/206.19; 128/206.21; 128/207.11
[58] Field of Search .................. 128/206.12, 206.13, 128/206.16, 206.17, 206.19, 206.21, 206.22, 206.24, 206.27, 207.11

[56] References Cited

U.S. PATENT DOCUMENTS

| D. 249,072 | 8/1978 | Revoir | D29/8 |
|---|---|---|---|
| D. 285,733 | 9/1986 | Cooper | D29/6 |
| D. 319,111 | 8/1991 | Sandel | D29/9 |
| D. 327,141 | 6/1992 | Hubbard et al. | D29/9 |
| 1,987,922 | 1/1935 | Blatt | 128/206.19 |
| 2,012,505 | 8/1935 | Goldsmith | 128/206.19 |
| 2,116,241 | 5/1938 | Heumann | 128/206.19 |
| 2,248,477 | 7/1941 | Lombard | 128/207.11 |
| 2,462,005 | 2/1949 | Schauweker | 128/146 |
| 2,494,406 | 1/1950 | Reitano | 128/146 |
| 2,762,368 | 9/1956 | Bloomfield | 128/146 |
| 3,170,461 | 2/1965 | Watts, Jr. | 128/146 |
| 3,220,409 | 11/1965 | Liloia et al. | 128/206.19 |
| 3,288,138 | 11/1966 | Sachs | 128/139 |
| 3,316,904 | 5/1967 | Wall et al. | 128/146.6 |
| 3,620,214 | 11/1971 | Thackston | 128/146.2 |
| 3,664,335 | 5/1972 | Boucher et al. | 128/206.19 |
| 3,688,768 | 9/1972 | Reimschussel et al. | 128/146.2 |
| 3,779,244 | 12/1973 | Weeks, Jr. et al. | 128/146.2 |
| 3,929,135 | 12/1975 | Thompson | 128/287 |

(List continued on next page.)

FOREIGN PATENT DOCUMENTS

| 527091 | 3/1981 | Australia. | |
|---|---|---|---|
| 0391726 | 10/1990 | European Pat. Off. | B01D 39/14 |
| 606686 | 7/1994 | European Pat. Off. | |
| 892262 | 3/1962 | United Kingdom | 128/206.19 |
| 2028664 | 3/1980 | United Kingdom | A62B 23/00 |
| 2059782 | 4/1981 | United Kingdom | 128/206.19 |
| 2103491 | 2/1983 | United Kingdom | A62B 7/10 |
| 8103266 | 11/1981 | WIPO | A41D 13/00 |
| 8900874 | 2/1989 | WIPO | A62B 18/02 |
| 8910106 | 11/1989 | WIPO | 128/206.19 |
| 9108829 | 6/1991 | WIPO. | |

OTHER PUBLICATIONS

U.S. Patent Application No. 08/499063, filed Jul. 6, 1995, and entitled, *Disposable Face Mask With Enhanced Fluid Barrier*.
U.S. Patent Application No. 08/491137, filed Jul. 17, 1995, and entitled, *Disposable Aerosol Mask With Face Shield*.
Australian Industrial Property Organization (AIPO) letter of Jul. 12, 1995.

(List continued on next page.)

*Primary Examiner*—Kimberly L. Asher
*Attorney, Agent, or Firm*—Baker & Botts, L.L.P.

[57] ABSTRACT

A face mask is provided that includes a filter body capable of filtering liquids, particles and aerosols of a size appropriate for the mask's intended purposes, while providing excellent breathability and comfort for extended periods of time. The filter body may be formed from multiple layers of filtration material having a generally rectangular configuration with a plurality of pleats. The mask may be secured to the head of a wearer by tie strips attached to flaps extending from the filter body to form a fluid seal between the periphery of the mask and the wearer's face. For some applications, the flaps may be formed from resilient or stretchable material which further enhances both the fluid seal formed by the mask and comfort for the wearer. A clear visor may also be attached to the mask to protect the wearer's eyes and portions of the wearer's face not covered by the mask.

27 Claims, 5 Drawing Sheets

U.S. PATENT DOCUMENTS

| | | | |
|---|---|---|---|
| 3,932,153 | 1/1976 | Byrns | 55/511 |
| 3,953,566 | 4/1976 | Gore | 264/288 |
| 3,971,369 | 7/1976 | Aspelin et al. | 128/146.2 |
| 3,971,373 | 7/1976 | Braun | 128/146.2 |
| 3,985,132 | 10/1976 | Boyce et al. | 128/146.2 |
| 4,187,390 | 2/1980 | Gore | 174/102 |
| 4,215,682 | 8/1980 | Kubik et al. | 128/205.29 |
| 4,319,567 | 3/1982 | Magidson | 128/206.19 |
| 4,323,063 | 4/1982 | Fisichella | 128/139 |
| 4,384,577 | 5/1983 | Huber et al. | 128/206.19 |
| 4,417,575 | 11/1983 | Hilton et al. | 128/206.19 |
| 4,419,993 | 12/1983 | Petersen | 128/201.15 |
| 4,419,994 | 12/1983 | Hilton | 128/206.19 |
| 4,454,881 | 6/1984 | Huber et al. | 128/206.15 |
| 4,495,030 | 1/1985 | Giglia | 128/206.19 |
| 4,510,931 | 4/1985 | Henderson et al. | 128/202.28 |
| 4,536,440 | 8/1985 | Berg | 428/284 |
| 4,547,420 | 10/1985 | Krueger et al. | 428/229 |
| 4,551,378 | 11/1985 | Carey, Jr. | 428/198 |
| 4,600,002 | 7/1986 | Maryyanek et al. | 128/206.19 |
| 4,606,341 | 8/1986 | Hubbard et al. | 128/206.19 |
| 4,616,647 | 10/1986 | McCreadie | 128/206.19 |
| 4,635,628 | 1/1987 | Hubbard et al. | 128/201.17 |
| 4,641,645 | 2/1987 | Tayebi | 128/206.19 |
| 4,662,005 | 5/1987 | Grier-Idris | 2/9 |
| 4,688,566 | 8/1987 | Boyce | 128/206.19 |
| 4,797,956 | 1/1989 | Boyce | 2/431 |
| 4,802,473 | 2/1989 | Hubbard et al. | 128/206.16 |
| 4,807,619 | 2/1989 | Dyrud et al. | 128/206.16 |
| 4,827,924 | 5/1989 | Japuntich | 128/206.12 |
| 4,850,347 | 7/1989 | Skov | 128/206.16 |
| 4,856,509 | 8/1989 | Lemelson | 128/206.19 |
| 4,873,972 | 10/1989 | Magidson et al. | 128/206.12 |
| 4,883,052 | 11/1989 | Weiss et al. | 128/205.27 |
| 4,920,960 | 5/1990 | Hubbard et al. | 128/206.12 |
| 4,941,470 | 7/1990 | Hubbard et al. | 128/206.13 |
| 4,944,294 | 7/1990 | Borek, Jr. | 128/206.19 |
| 4,945,574 | 8/1990 | Dagher | 2/9 |
| 4,966,140 | 10/1990 | Herzberg | 128/206.19 |
| 4,969,457 | 11/1990 | Hubbard et al. | 128/206.12 |
| 5,003,633 | 4/1991 | Itoh | 2/9 |
| 5,012,805 | 5/1991 | Muckerheide | 128/205.28 |
| 5,020,533 | 6/1991 | Hubbard et al. | 128/206.23 |
| 5,025,506 | 6/1991 | Huang | 2/206 |
| 5,033,115 | 7/1991 | Bowling et al. | 2/51 |
| 5,035,240 | 7/1991 | Braun et al. | 128/205.27 |
| 5,094,236 | 3/1992 | Tayebi | 128/206.12 |
| 5,107,547 | 4/1992 | Scheu | 2/206 |
| 5,150,703 | 9/1992 | Hubbard et al. | 128/206.12 |
| 5,322,061 | 6/1994 | Brunson | 128/206.13 |
| 5,419,318 | 5/1995 | Tayebi | 128/206.24 |

OTHER PUBLICATIONS

European Search Report Dated May 10, 1995.

"DELTA Disposable Respirators" *Racal Health & Safety*, 1993 (4 pages).

The Mask Collection by Tecnol, Reprinted from *AORN Journal*, 1987.

R1050 AO Safety Products brochure, Dust Demon Foldable, Reusable/Disposable Respirator, 1989.

Glendale brochure, Dustbuster Comfort Plus Full Dust and Mist Protection, 7/92/10M.

(U.S. Patent # 4802473). Tecnol Fluidshield Brochure, "The First Mask Specifically Designed to Resist fluid Penetration".

Tecnol Fluidshield Brochure, "The Only Masks with Loncet Breathable Film . . . Your Extra Layer of Protection from Body Fluids." (U.S. patents 4920960, 4969457, 4802473, 4941479, 5020533, 5150703).

W. T. Davis, "Filtration Efficiency of Surgical Face Masks: The Need for More Meaningful Standards," *American Journal of Infection Control*, pp. 16–18.

FACE MASK WITH ENHANCED SEAL AND METHOD

TECHNICAL FIELD OF THE INVENTION

This invention relates in general to medical products, and in particular, but not by way of limitation, to a face mask with an enhanced seal to prevent fluids and aerosols from contacting the face of a wearer. Various types of visors or shields may be attached to the mask to prevent liquids from contacting the eyes of the wearer.

BACKGROUND OF THE INVENTION

Wearing protective face masks has become standard procedure for many health care and other related activities. The use of a face mask is important, for example, to lab technicians while conducting tests, to nurses during the care of patients, to physicians during surgery and other types of medical treatment, and to dentists working in a patient's mouth.

The rapid increase of infectious diseases, particularly AIDS, has made the use of such protective equipment increasingly important. The Center for Disease Control in Atlanta, Ga., has found that the AIDS virus (HIV) can be passed by contact with body fluids. Contact of AIDS contaminated body fluids with another person's source of body fluids, e.g., eyes, nose, mouth, etc., can pass the disease. Therefore, it is necessary to prevent a patient's body fluids from contacting the face of health care personnel.

During the past several years, health care personnel have become more aware of the potential hazards associated with airborne pathogens, such as the hepatitis B virus and infectious tuberculosis associated with many HIV patients. It has been found that aerosols having airborne liquid and solid particles are generated not only by the exhalation of infected patients, but also by certain procedural manipulations and processes that impart energy to microbial suspensions. Also many viral hemorrhagic fevers such as yellow fever, rift valley fever and perhaps rocky mountain spotted fever, rabies and smallpox can be transmitted through aerosols. A considerable number of studies have been made which are now beginning to identify the transmission of viruses through "non-accident" situations. Accordingly, there is an increased interest in a face mask which will form a complete fluid seal around the periphery of the mask and at the same time be easy to put on and comfortable to wear. Many face masks which are presently available allow the passage of fluids and/or aerosols between the periphery of the mask and the wearer's face.

One type of face mask is illustrated in U.S. Pat. No. 2,012,505 entitled Mask, issued on Aug. 27, 1935 to S. J. Goldsmith. Another type of face mask is illustrated in U.S. Pat. No. 4,319,567 entitled Disposable Face Mask, issued on Mar. 16, 1982 to M. Magidson. This mask is molded and has been especially configured in an effort to avoid leakage of fluid flow past the edges of the mask. Obviously, leakage cannot be tolerated when attempting to control liquids and aerosols. Typically surgical style pleated face masks may have less than an optimal fit to prevent the passage of liquids and/or aerosols between the periphery of the mask and a wearer's face. Recent developments in surgical face masks have resulted in improved resistance to liquid penetration from the exterior of such masks. U.S. Pat. No. 4,920,960 entitled Body Fluids Barrier Mask, issued on May 1, 1990 to Hubbard, et al., is exemplary of improvements in such masks.

SUMMARY OF THE INVENTION

In accordance with the present invention, an improved face mask is provided to substantially reduce or eliminate the shortcomings previously associated with surgical style face masks. A shield or visor may be attached to the improved face mask in accordance with one aspect of the present invention.

The present invention provides a surgical style face mask which inhibits the passage of fluids between the periphery of the mask and the wearer's face while providing enhanced comfort to the wearer. The present invention may be used with standard pleated style face masks, off-the-face style masks, or molded cone style masks. For some applications, a single pair of ties may be used to secure a mask incorporating the present invention with the head and face of the wearer. For other applications, a mask incorporating the present invention may be secured to the head and face of the wearer with a double pair of ties or four surgical tie strips. For still further applications, a mask incorporating the present invention may be secured to the head and face of the wearer with a continuous loop of resilient material. Fluid impervious flaps are included to extend the coverage area of the face mask and improve the fluid seal between the periphery of the mask and the face of the wearer. The fluid impervious flaps also allow reducing the amount of filter media associated with each face mask while maintaining the same amount of effective filtration area and breathability.

One aspect of the present invention provides a face mask having a filter body for covering the nose and mouth of a wearer. The filter body has top and bottom edges with the top edge arranged to extend across the bridge of the nose of the wearer and the bottom edge arranged to extend under the wearer's chin. Fluid impervious flaps extend from each side of the filter body for use in attaching the mask to the wearer's face and to provide an enhanced fluid seal between the periphery of the mask and the wearer's face. A securing means may be attached to the respective flaps extending from each side of the filter body. The securing means may be extended over the head of the wearer for use in urging the top and bottom edges of the filter body and the flaps on each side of the filter body into tight engagement with the wearer's face to prevent undesired fluid flow between the periphery of the mask and the wearer's face. The securing means may preferably be formed from resilient material to provide comfort to the wearer while maintaining a tight peripheral seal for long periods of time. The securing means may be formed from other types of material as desired. For one application of the present invention, a first and second securing means associated with each flap may be crossed over each other to further enhance the fluid seal formed by the periphery of the mask with the wearer's face.

Another aspect of the present invention provides a face mask having a plurality of layers of selected material which are resistant to the passage of aerosols and/or liquids from the exterior of the mask to the face of the wearer. One or more of these layers may be formed from expanded polytetraflouroethylene (PTFE).

A significant technical advantage of the present invention includes a face mask having a filter body with fluid impervious flaps which cooperate with tie strips to allow the mask to conform to the contours of the face of a wearer. The filter body and the flaps block liquid spray and aerosols from contacting the portions of the wearer's face covered by the mask. The present invention allows optimizing the filtration capability of the mask for resistance to the passage of liquids and/or aerosols while allowing for a substantially improved fit between the periphery of the mask and the contours of a wearer's face. An optically clear visor may be attached to the filter body to protect the wearer's eyes and portions of the wearer's face which are not covered by the mask.

Another significant technical advantage of the present invention includes a face mask having a filter body with fluid impervious flaps which allow reducing the surface area of the filter body, if desired, and thus the amount of filter media used to manufacture the mask while maintaining the same or an even greater amount of coverage over the face of the wearer. The fluid impervious flaps allow reducing the amount of filter media used in construction of the mask, if desired, while maintaining the same high degree of breathability and high efficiency for removing particulate matter and/or aerosols.

A still further technical advantage of the present invention includes a face mask having a filter body with a plurality of pleats formed in the filter media with at least one of the pleats folded in a reverse direction as compared to the other pleats. The reverse pleat in cooperation with the other pleats helps to hold the filter body away from the face of the wearer to increase breathing comfort while wearing the mask for long periods of time.

BRIEF DESCRIPTION OF THE DRAWINGS

For a more complete understanding of the present invention and for the further advantages thereof, reference is now made to the following description taken in conjunction with the accompanying drawings, in which.

DETAILED DESCRIPTION OF THE INVENTION

The preferred embodiments of the present invention and its advantages are best understood by referring to FIGS. 1–9 of the drawings, like numerals being used for like and corresponding parts of the various drawings.

Face mask 12 incorporating the present invention retards the flow of bacteria, liquids and aerosols from the exterior of mask 12 to the nose and mouth of wearer 14. For purposes of this application, aerosols are defined as insoluble liquids or particulate matter frequently associated within microbial solutions. The term "fluid" is used within this application to include any gas, liquid, or mixture of gas and liquid. Particulate matter and aerosols may be entrained with such fluids.

The present invention allows optimizing the fluid barrier formed between the periphery of mask 12 and the face of wearer 14 and the filtration capability of mask 12 to resist the passage of liquids, particulate matter and/or aerosols while at the same time minimizing resistance to normal breathing of wearer 14. The present invention allows using one layer or multiple layers of filter media which may be specifically designed to block the passage of aerosols in addition to liquids.

Fastening devices or securing means, such as tie strips 16 and 18, may be used to removably attach mask 12 to the head and face of wearer 14. Tie strips 16 and 18 are preferably secured to mask 12 at respective bonded areas 20 and 22. Portions 16a and 18a extending from their respective bonded areas 20 and 22 provide a first pair of ties for securing mask 12 to the face of wearer 14. Portions 16b and 18b extending from their respective bonded areas 20 and 22 provide a second pair of ties for securing mask 12 to the face of wearer 14.

As will be explained later in more detail, various types of securing means may be used to attach a mask incorporating the present invention to the face of a wearer. Tie strips 116 and 118 shown in FIGS. 3–8 represent one of these alternative securing means. Also, elastic ear loops, such as shown in U.S. Pat. No. 4,802,473 entitled Face Mask with Ear Loops, may be satisfactorily used with the present invention. U.S. Pat. No. 4,802,473 is incorporated by reference for all purposes within this application. As shown in FIG. 8, tie strips 16 and 18 may be replaced by a continuous loop of resilient material which is disposed within but not bonded to flaps 30 and 32.

Figure 1:
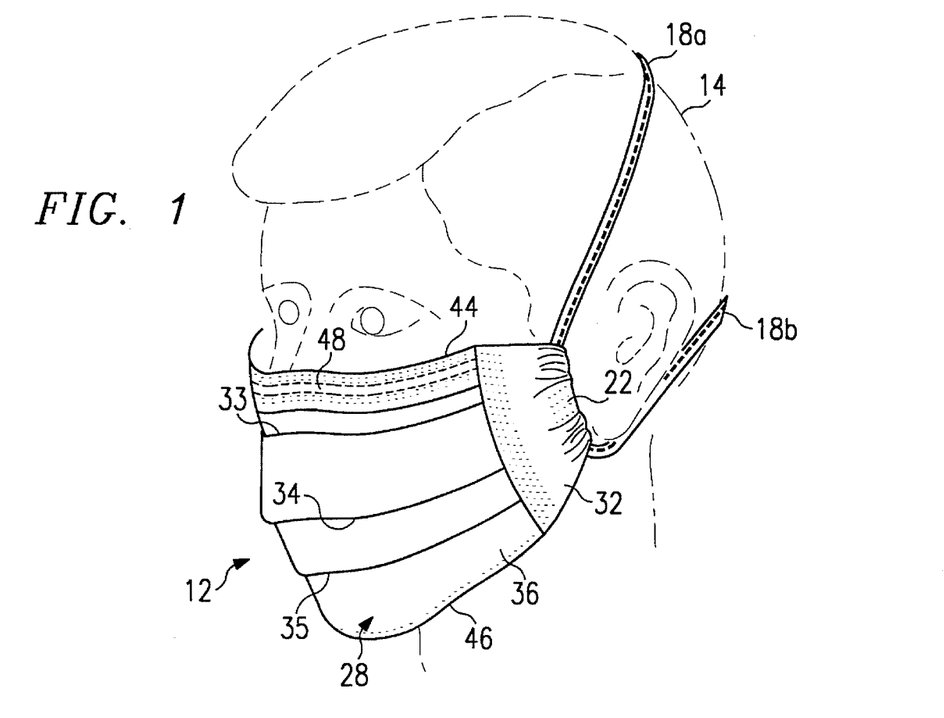
FIG. 1 is a perspective view of a face mask and filter body incorporating one embodiment of the present invention illustrated on the head of a wearer.
Figure 2:
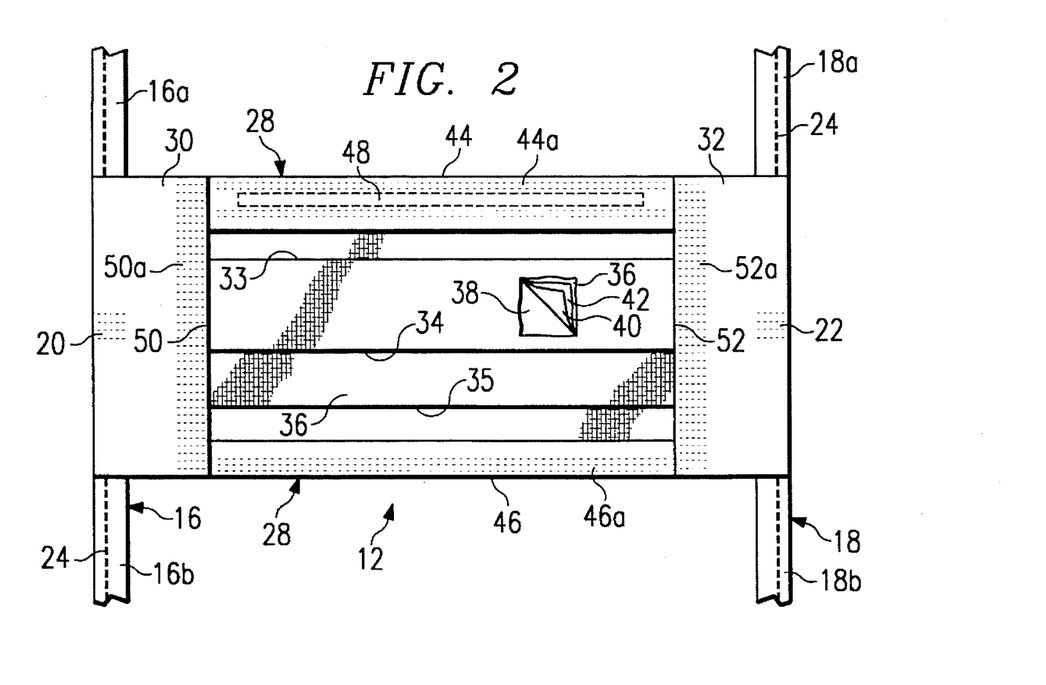
FIG. 2 is an elevational view with portions broken away of the mask of FIG. 1 with a cut-a-way showing four layers of material used to form the filter body of the mask.

As best shown in FIGS. 1 and 2, mask 12 includes filter body 28 with flaps 30 and 32 extending respectively from each side of filter body 28. For some applications, filter body 28 may be fabricated in general as described in U.S. Pat. No. 4,635,628 entitled Surgical Face Mask with Improved Moisture Barrier and U.S. Pat. No. 4,969,457 entitled Body Fluids Barrier Mask. Both of these patents are incorporated by reference for all purposes within this application.

Flaps 30 and 32 are preferably formed from fluid impervious material folded with a generally U-shaped cross section. Flaps 30 and 32 may sometimes be referred to as C-folds. For one application of the present invention, flaps 30 and 32 may be formed from polyethylene film laminated to any non-woven material. The non-woven material may also be hydro-entangled. For other applications, the polyethylene film may be laminated to any type of material as desired. The polyethylene film layer may be color coded to correspond with different applications for using the resulting face mask.

For other applications, a breathable type film may be used to form flaps 30 and 32. For still further applications, flaps 30 and 32 may be formed from resilient and/or stretchable materials. Such resilient materials include thermoplastic rubbers which may be extruded or injection molded as strips or sheets of material. An example of such thermoplastic rubbers is available under the trademark KTON® from Shell Oil Company.

One of the benefits of the present invention is the ability to form flaps 30 and 32 from materials that have lower cost as compared to the material used to form filter body 28. Another benefit of the present invention is the ability to form flaps 30 and 32 from a wide variety of materials which provide an enhanced fluid seal with the face of the wearer while providing a comfortable fit during long periods of use. Such materials are available from various suppliers.

Filter body 28 and flaps 30 and 32 are preferably designed to prevent or retard the passage of liquids from the exterior of mask 12 to the face of wearer 14. It is extremely difficult to construct a mask that will fit the facial configuration of all wearers without constructing the mask specifically for each individual face. The use of flaps 30 and 32 greatly increases the different sizes and types of faces which can be effectively protected by mask 12. Forming flaps 30 and 32 from suitable resilient or stretchable material further improves facial fit with a large number of wearers.

Filter body 28 comprises a plurality of pleats 33, 34 and 35 which allow expansion of filter body 28 to cover the mouth and nose of wearer 14. The number of pleats 33, 34 and 35 formed in filter body 28 may be varied to provide the desired fit with the face of wearer 14. Pleat 33 is preferably folded in a reverse direction as compared to pleats 34 and 35. By providing reverse pleat 33, filter body 28 has an increased tendency to stand away from the face of wearer 14.

For some applications filter body 28 may be formed without pleats. For other applications, filter body 28 may be formed with non-collapsing face panels such as shown in U.S. Pat. No. 4,606,341 entitled Non-Collapsible Surgical Face Mask. U.S. Pat. No. 4,606,341 is incorporated by reference for all purposes within this application. For still further applications, filter body 28 may be formed from only one layer of material or from multiple layers of material. Flaps 30 and 32 allow for a wide variety of options in selecting material with the desired breathability and fluid resistance for filter body 28.

The use of reverse pleat 33 in cooperation with pleats 34 and 35 forms a larger breathing chamber as compared to other soft, pleated style masks which contact a substantial portion of the wearer's face. The larger breathing chamber permits cooler and easier breathing associated with "off-the-face" style mask such as shown in U.S. Pat. No. 4,606,341. The present invention allows optimizing the volume of air contained within filter body 28 without sacrificing comfort to the wearer or filtration efficiency.

If the breathing chamber foiled by filter body 28 is too large, excessive amounts of exhaled air may be retained within filter body 28 at normal breathing rates. By properly selecting the size of filter body 28 and flaps 30 and 32, excessive heating of air within filter body 28 is minimized and dizziness from prolonged periods of re-breathing exhaled air is also minimized. Since the present invention results in an enhanced fluid seal or barrier between the periphery of mask 12 and the face of wearer 14, incorporating the benefits of an "off-the-face" style face mask are important for extended periods of wearing mask 12.

As shown by the cutaway portion of FIG. 2, filter body 28 includes four layers of material with an external surface of cover stock 36 as the outermost layer. Inner layer or internal surface 38 which contacts the face of wearer 14 may be constructed of a light weight, highly porous, softened, non-irritating, non-woven fabric, such as Dexter, Inc. product No. 3768. Inner layer 38 is designed to prevent unwanted materials such as facial hair, loose fibers or perspiration from contacting intermediate layers 40 and 42 which might cause a wicking effect to draw liquids through filter body 28. Inner layer 38 also provides a comfortable surface for contact with the face of wearer 14.

Intermediate layer 40 preferably comprises a barrier material that is capable of differentiating between gases and liquids and may be, for example, Visqueen Film Products' low density polyethylene, Vispore X-6212. Non-wetting materials, such as used to form barrier material 40, have small apertures which prevent liquids with a relatively high surface tension from passing therethrough yet will allow gases with a low surface tension to pass therethrough. It is preferable o have the apertures as large as possible to allow easy breathing, and yet small enough to retard or prevent the flow of liquids. Intermediate layer 40 is designed to freely pass gases in either direction, while restricting the passage of liquids in at least on direction. Filter body 28 is constructed with barrier material 40 positioned to restrict liquid passage from the exterior of mask 12. Further description of the construction and operation of such barrier material may be found in U.S. Pat. No. 3,929,135 issued Dec. 30, 1975, to Thompson, assigned to Proctor and Gamble Co., and is incorporated by reference for all purposes.

The next intermediate layer is preferably filtration media 42, which may be, for example, melt blown polypropylene or polyester. Filtration media 42 is provided to inhibit the passage of airborne bacteria in either direction which will prevent passage of germs to and from wearer 14. Outermost layer 36 provides the external surface for filter body 28, which may be treated, for example, by spraying with a liquid repellant to render the external surface material resistant to liquids.

Outer layer 36 and filtration media layer 42 serve as an aid to barrier material 40 by slowing down any liquid that may be splashed, sprayed or thrown at mask 12. By requiring the liquid to pass through layers 36 and 42 prior to reaching barrier material 40, the liquid will have less pressure and barrier material 40 will be better able to prevent passage of the liquid. Outer layer 36 may be formed from non-woven material such as cellulose fiber.

Filter body 28 may be formed by bonding layers 36, 38, 40, and 42 with each other in a generally rectangular configuration. Such bonding is preferably provided along top edge 44, bottom edge 46 and lateral sides 50 and 52, respectively. The corresponding bonded areas 44a, 52a, 46a, and 50a may be formed by sewing, glue, heat sealing, welding, ultrasonic bonding and/or any other suitable bonding procedure. Flaps 30 and 32 are preferably integrally attached to filter body 28 as part of the respective bonded areas 50a and 52a. Flaps 30 and 32 are preferably formed from fluid impervious material such as a plastic membrane and folded with a U-shaped configuration to form an opening to receive tie strips 16 and 18 therein. Bonded areas 20 and 22 are preferably used to secure the approximate mid-point of tie strips 16 and 18 with corresponding mid-points of flaps 30 and 32.

For some applications, flaps 30 and 32 may be formed with a J-shaped configuration to receive tie trips 16 and 18 therein. Also, bonded areas 20 and 22 may be replaced by other types of restrictions to hold tie strips 16 and 18 within their respective flaps 30 and 32. The fluid seal between the sides of filter body 28 and the wearer's face may be enhanced by reducing the size of bonded areas 20 and 22, or by replacing bonded areas 20 and 22 with other suitable restrictions to retain tie strips 16 an 18 within their respective flaps 30 and 32.

Top edge 44 of filter body 28 preferably includes an elongated malleable member 48 provided so that top edge 44 of filter body 28 can be configured to closely fit the contours of the nose and cheeks of wearer 14. Malleable member 48 is preferably constructed from an aluminum strip with a rectangular cross section, but may also be a molded or malleable steel or plastic member. Top edge 44, bottom edge 46 and flaps 30 and 32 cooperate with each other to define the periphery of mask 12 which contacts the face of wearer 14. Flaps 30 and 32 substantially increase the area of contact with the face of wearer 14 as compared to a face mask having only lateral sides 50 and 52 in contact the face of wearer 14.

Typically surgical style pleated face masks have a generally rectangular or square configuration of approximately seven inches by seven inches prior to pleating. The length and width dimensions of a typical face mask may vary by plus or minus one-half an inch (±½) resulting in a face mask which is often rectangular in configuration as compared to a square. For some applications, the present invention allows reducing the length of top edge 44 from seven inches to as short as four and one-half to five inches. Alternatively, the present invention allows increasing the length of top edge 44 as desired. Also, the distance from top edge 44 to bottom edge 46 when mask 12 has been placed over the face of wearer 14 may be reduced from seven inches to five and one-half to six inches. Therefore, flaps 30 and 32, along with other features of the present invention allow reducing the total area of the filter media associated with mask 12 from approximately forty-nine square inches to twenty-five square inches to thirty square inches while maintaining approximately the same effective area. This reduction in area results in a substantial savings in the cost of materials used to fabricate mask 12 while, at the same time, maintaining good breathability, high efficiency filtration, and providing an improved seal between the periphery of mask 12 and the face of wearer 14.

Surgical ties 16 and 18 may be formed from various types of material. For one application of the present invention surgical ties 16 and 18 are preferably formed from thermally bonded polypropylene having a basis weight of 1.5 to 1.65 ounces per square yard. This particular type of material can be ultrasonically welded, stitched or heat and pressure bonded in various patterns to provide a resilient securing means for use in attaching mask 12 to the face of wearer 14.

As shown in FIG. 2, a single sonic stitch 24 is provided along the length of each surgical tie 16 and 18 to provide the desired longitudinal stretch and recovery capability. Single sonic stitch pattern 24 allows most of the material used to form surgical ties 16 and 18 to be open and free from the associated bonded area. Stitch pattern 24 allows surgical ties 16 and 18 to retain their naturally resilient characteristics.

Various other types of resilient material may be satisfactorily used to form surgical ties 16 and 18. By providing resilient surgical ties 16 and 18, the periphery of face mask 12 will maintain a tight fluid barrier with the face of wearer 14 over a relatively long period of time. Talking and other activities by wearer 14 will not compromise the integrity of the resulting fluid barrier. Laminated strips of material may also be used to form ties 16 and 18.

Figure 9:
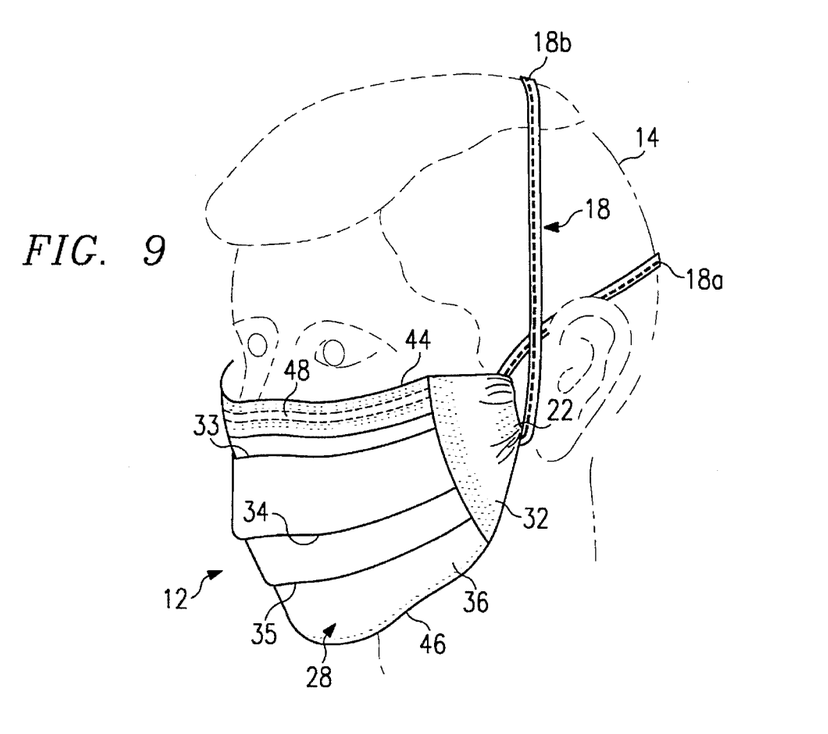
FIG. 9 is a perspective view showing an alternative embodiment of the present invention for attaching the face mask and filter body of FIG. 1 to the head of a wearer.

The arrangement of surgical ties 16 and 18 is such that portions 16a and 18a extending from top edge 44 may be placed over the top of the head of wearer 14. Portions 16b and 18b extending from bottom edge 46 may be positioned around the lower base of the head of wearer 14 as illustrated in FIG. 1. Positioning tie strips 16 and 18 in this manner results in compressing or gathering the respective flaps 30 and 32 to form a flat, flange type fluid barrier with the face of wearer 14. Also, securing surgical ties 16 and 18 in this manner urges top edge 44 and bottom edge 46 into fluid sealing engagement with the contours of the face of wearer 14. Surgical tie strips 16a, 18a, 16b and 18b may be positioned on the head of wearer 14 to provide the optimum pull angle and the optimum amount of force to form the desired fluid barrier between the periphery of mask 12 and the face of wearer 14. An alternative arrangement for tie strips 16 and 18 is shown in FIG. 9.

Figure 3:
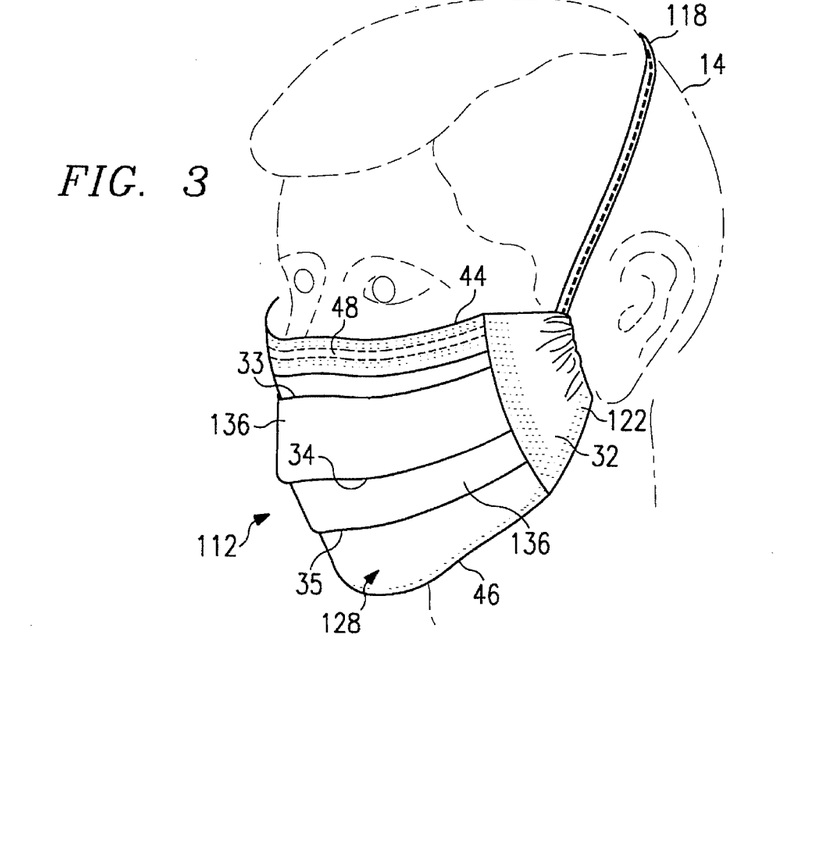
FIG. 3 is a perspective view of a face mask and filter body incorporating another embodiment of the present invention illustrated on the head of a wearer.
Figure 4:
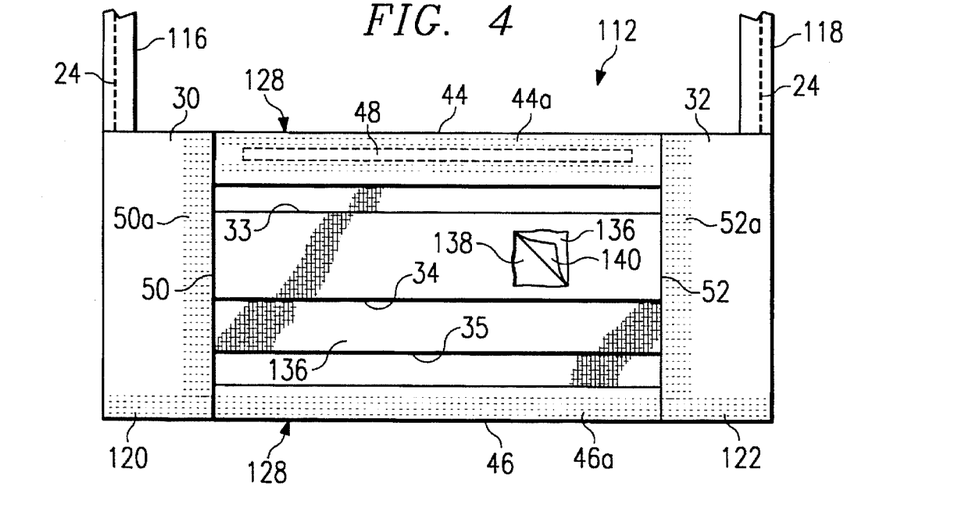
FIG. 4 is an elevational view with portions broken away of the mask of FIG. 3 with a cut-a-way showing three layers of material which form the filter body of the mask.

An alternative embodiment of the present invention is represented by mask 112 shown in FIGS. 3 and 4. Masks 12 and 112 are similar except for the configuration of tie strips 116 and 118 and different layers of material used to form filter body 128. Flaps 30 and 32 are attached to filter body 128 in the same manner as previously described for mask 12. However, one end of tie strip 116 is inserted into flap 30 and attached thereto at bonded area 120. In similar manner, tie strip 118 is placed within flap 32 and bonded at area 122. Thus, when bottom edge 46 of filter body 128 is placed under the chin of wearer 14, tie strips 116 and 118 compress or gather the respective flaps 30 and 32 to form a fluid barrier with the adjacent portion of the face of wearer 14.

For many applications, tie strips 116 and 118 in cooperation with flaps 30 and 32 provide a fluid barrier between the periphery of mask 112 and the face of wearer 14 which is equivalent to the fluid barrier resulting from the use of four tie strips 16a, 18a, 16b and 18b of mask 12. For some applications tie strips 116 and 118 could be a single strip of resilient material extending from bonded area 120 through flaps 30 and 32 to bonded area 122.

As illustrated in FIG. 4, filter body 128 includes an outer mask layer 136 that is preferably constructed from a spunbonded polypropylene. Outer mask layer 136 may also be constructed from a bi-component and/or powder bonded material such as polyethylene or polypropylene, a cellulastic tissue, or a spun-bonded polyester. Outer mask layer 136 will typically have a basis weight range of 0.5 ounces per yard of 1.0 ounces per yard. 0.7 ounces per yard is one of the preferred basis weights for outer layers 136.

Inner mask layer 138 is preferably composed of bicomponent polyethylene and polypropylene or bicomponent polyethylene and polyester. Layer 138 may also be constructed from polyester and/or polyethylene material or cellulastic tissue. Layer 138 will typically have a basis weight range of 0.4 ounce per yard to 0.75 ounces per yard. 0.413 ounces per yard is one of the preferred basis weights for layer 138. One or more intermediate layers of filter media may be disposed between outer mask layer 138 and inner mask layer 138. Selection of the number and type of intermediate layers of filter media will depend upon the intended use and function for mask 112. In FIG. 4, filter body 128 is shown with only one intermediate mask layer 140 which comprises the filter media for mask 112. This layer is preferably constructed from a melt-blown polypropylene, but may be constructed from an extruded polycarbonate, a melt-blown polyester, or a melt-blown urethane.

Figure 5:
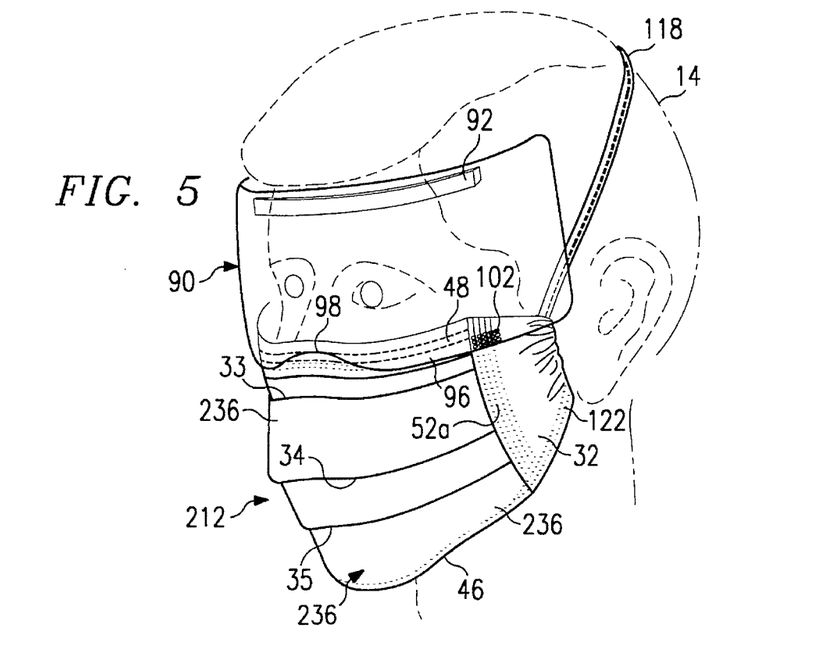
FIG. 5 is a perspective view of a face mask and visor incorporating a further embodiment of the present invention illustrated on the head of a wearer.
Figure 6:
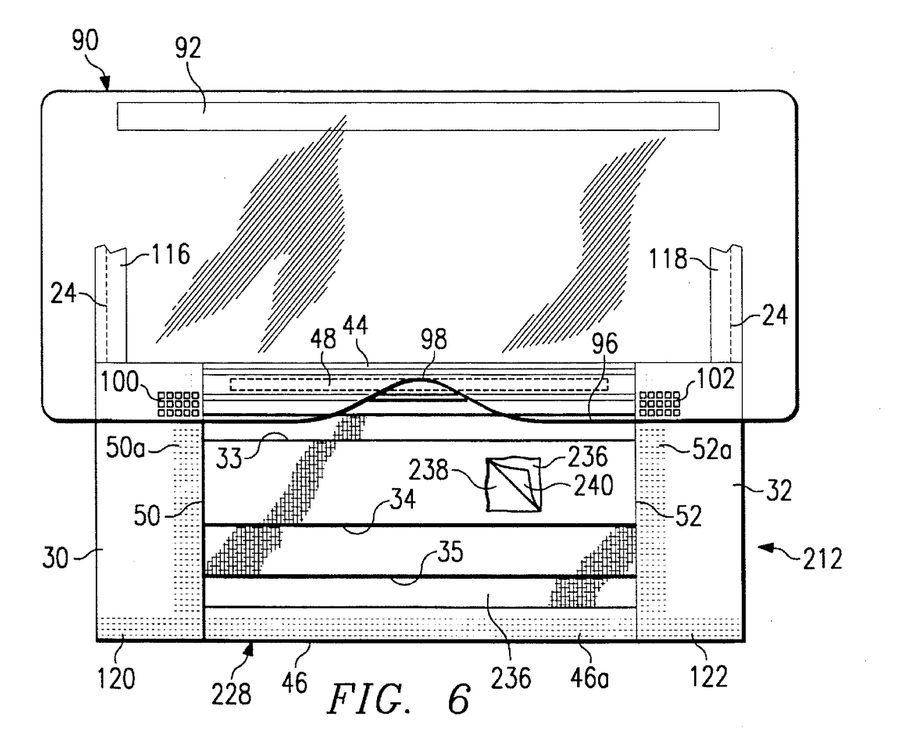
FIG. 6 is an elevational view with portions broken away of the mask and visor of FIG. 5 with a cut-a-way showing three layers of material which form the filter body of the mask.

Another alternative embodiment of the present invention is represented by mask 212 with attached visor 90 as shown in FIGS. 5 and 6. Mask 212 includes filter body 228 which may be secured to wearer 14 by securing means 116 and 118 as previously described for mask 112. Filter body 228 is similar to previously described filter body 28 and filter body 128 except for the different layers of material used to form filter body 228. An important benefit of the present invention includes the ability to select various types of material to form the flaps and filter body associated with each mask 12, 112, and 212.

For the embodiment of the present invention shown in FIG. 6, filter body 228 includes intermediate layer 240 of filter media disposed between layers 236 and 238. For this particular embodiment, inner and outer mask layers 238 and 236 respectively are formed from the same type of material. However, various types of material may be used with intermediate mask layer 240. For the embodiment of FIG. 6, intermediate mask layer 240 may be formed from an expanded polytetrafluoroethylene (PTFE) membrane. Such materials are manufactured by W. L. Gore & Associates. A more complete description of the construction and operation of such materials can be found in U.S. Pat. No. 3,953,566 entitled Process for Producing Porous Products, issued on Apr. 27, 1976 to Robert W. Gore, and U.S. Pat. No. 4,187,390 entitled Porous Products for Process Therefor, issued on Feb. 5, 1980 to Richard W. Gore. These patents are incorporated by reference for all purposes within this application. For some applications and operating environments the use of filter media 240 substantially enhances the performance of mask 212 in an aerosol environment.

Face shield or visor 90 preferably comprises a clear, plastic film such as polyester or polyethylene. Visor 90 is generally dimensioned to fit across the portions of the face of wearer 14 which are not covered by mask 212. Visor 90 is specifically positioned on filter body 228 to protect the eyes of wearer 14 from liquid spray and liquid splashes. The plastic material comprising visor 90 may have a thickness of approximately 0.005 inches with enough stiffness to prevent collapse and yet having sufficient flexibility to bend and conform generally with the face of wearer 14. As will be explained later, visor 90 is preferably bonded of filter body 28 near the opposite ends of top edge 44.

Visor 90 preferably has a generally rectangular configuration with rounded corners. The length of visor 90 is preferably selected to be slightly larger than the length of mask 212. The width of visor 90 is selected to be approximately equal to the width of filter body 228 when expanded over the nose and mouth of wearer 14. Foam pad 92 is provided near the top of visor 90 to position visor 90 away from the face of wearer 14. For some applications, foam pad 92 may not be required for proper fit of visor 90.

Lower edge 96 of visor 90 preferably includes notch 98 which allows visor 90 to conform with the nose and face of wearer 14 without causing creases or wrinkles in visor 90. The dimensions of mask 212, filter body 228 and visor 90 may be modified to accommodate wearers having smaller or larger facial features. If desired, a darkened strip of material (not shown) may be placed along top edge 44 of filter body 228 to reduce glare associated with using visor 90. U.S. Pat. No. 5,020,533 entitled Face Mask with Liquid and Glare Resistant Visor describes the benefits of using such a darkened strip of material. U.S. Pat. No. 5,020,533 is incorporated by reference for all purposes within this application.

Visor 90 is preferably attached to filter body 228 near the opposite ends of top edge 44 proximate to the attachment of flaps 30 and 32 with filter body 228. Bonded areas 100 and 102 are preferably used to secure visor 90 to filter body 228 at these locations. Various adhesives, ultrasonic seals and/or heat seals may be used to establish bonded areas 100 and 102. Ultrasonic seals (sometimes referred to as ultrasonic welding) may be particularly advantageous for attaching visor 90 to filter body 228. Bonded areas 100 and 102 cooperate to allow visor 90 to easily adapt to the contours of the face of wearer 14. Notch 98 in lower edge 96 along with bonded areas 100 and 102 prevent visor 90 from moving up with respect to mask 212 and forming a gap therebetween. Blow-up associated with normal breathing of wearer 14 and the resulting fogging of visor 90 is substantially eliminated by properly selecting the dimensions and location of malleable strip 48 with respect to top edge of 44. Malleable strip 48 is preferably positioned in the center of the top edge 44.

The present invention allows designing mask 212 with the optimum periphery to fit the face of wearer 14, the optimum dimensions for malleable strip 48 to form an enhanced fluid barrier with the nose and face of wearer 14, and the optimum position for visor 90 with respect to the eyes and uncovered portion of the face of wearer 14. The present invention allows modification to the length of top edge 44 and bottom edge 46 while maintaining the required surface area for efficient filtration and normal breathing through filter media 240.

The use of barrier materials which block the passage of liquids is particularly important when mask 212 with visor 90 is worn in an environment where wearer 14 may be exposed to "body fluids." These fluids such as blood, urine and saliva may contain highly contagious germs and viruses. Contact of AIDS-contaminated body fluids with another person's source of body fluids, such as the eyes, nose and mouth, may transmit the disease. Therefore, it is often preferable to include layer 40 and/or 240 which are resistant to the passage of liquids through filter body 228 to prevent body fluids from contacting the nose and mouth of wearer 14.

U.S. Pat. Nos. 4,920,960 and 5,020,533 provide additional information on materials which may be used for layers 36, 38, 40, 42, 136, 138, 140, 236, 238 and 240 and face masks constructed with such materials. Other types of liquid barriers may be satisfactorily used with the present invention.

Referring to FIG. 5, mask 212 is illustrated as being located on the face of wearer 14. Top edge 44 with malleable member 48 and lower edge 96 of visor 90 conform very closely to the configuration of the nose and cheeks of wearer 14. It is important that bottom edge 46 and the chin of wearer 14 and top edge 44 and the nose and cheeks of wearer 14 fit very closely since any leaks result in bypass or blow-by of fluids either entering mask 212 or being discharged from mask 212 during use by wearer 14. Also, leakage around top edge 44 may cause fogging of visor 90.

Accordingly, resilient surgical ties 116 and 118 have one end attached at bonded areas 120 and 122 respectively as shown in FIGS. 5 and 6. The arrangement is such that ties 116 and 118 can be placed over the top of the head of wearer 14, as illustrated in FIG. 5, and force applied to compress or gather the respective flaps 30 and 32. This force urges bottom edge 46 into sealing engagement with the chin of wearer 14. At the same time, compressing flaps 30 and 32 applies force to top edge 44 which tends to move top edge 44 into tighter sealing engagement with the nose and cheeks of wearer 14. The position of ties 116 and 118 and filter body 228 in cooperation with flaps 30 and 32 results in the optimum pull to form a fluid tight barrier or seal between the periphery of mask 212 and the face of wearer 14.

Figure 7:
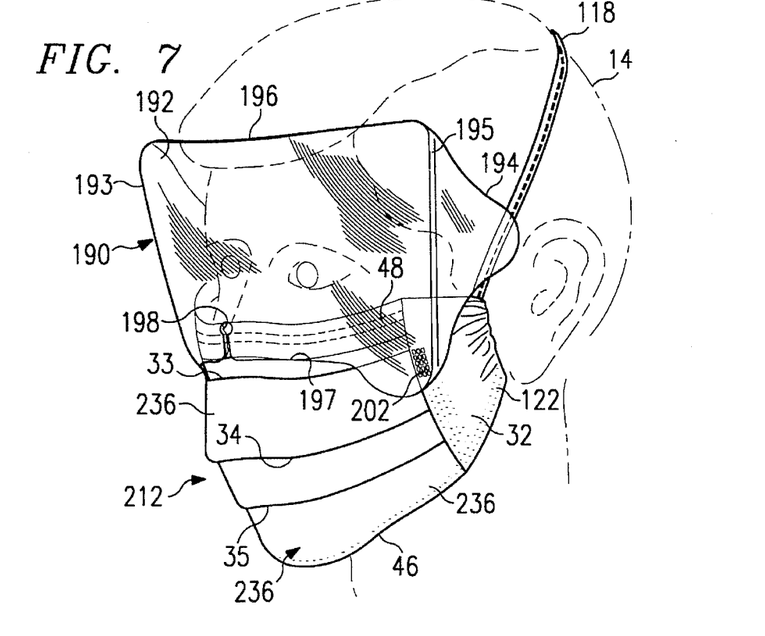
FIG. 7 is a perspective view of a face mask and visor incorporating a still further embodiment of the present invention illustrated on the head of a wearer.
Figure 8:
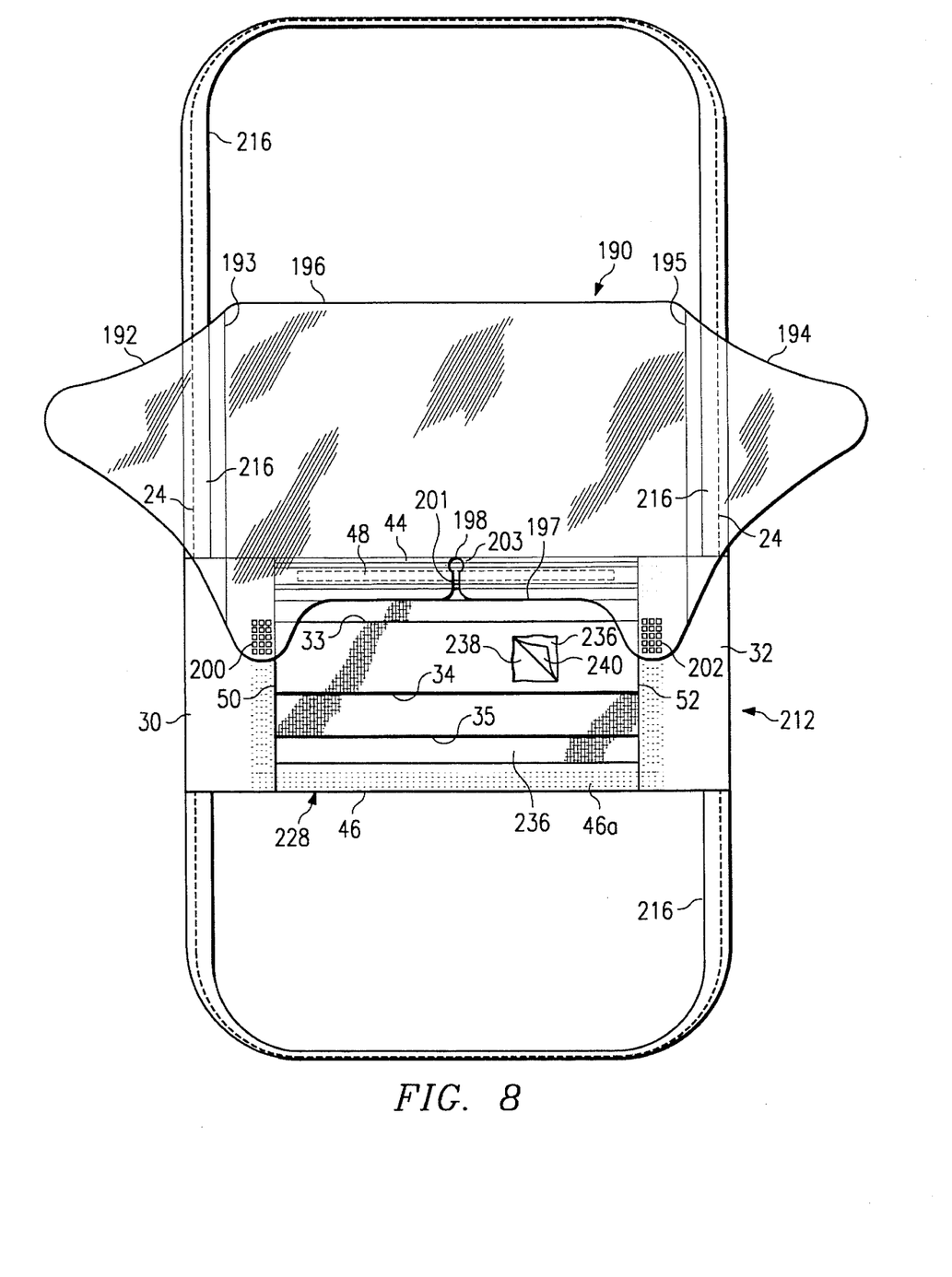
FIG. 8 is an elevational view with portions broken away of the mask and visor of FIG. 7 with a cut-a-way showing an alternative securing means for attaching the mask and visor to the head of a wearer.

A still further embodiment of the present invention is represented by mask 212 with attached visor 190 as shown in FIGS. 7 and 8. If desired, visor 190 could be attached to mask 12 or mask 112. Face shield or visor 190 preferably comprises a clear, plastic film such as polyester or polyethylene. Visor 190 is generally dimensioned to fit across the length of mask 212 and to extend over the eyes of wearer 14.

Visor 190 preferably includes foldable side extensions 192 and 194. Foldable side extensions 192 and 194 are an integral part of and extend from main body 196 of visor 190. Edges 193 and 195 of main body 196 are preferably scored or creased to allow flexible movement of the respective side extensions 192 and 194 relative to main body 196. As best shown in FIG. 7 side extensions 192 and 194 cooperate with main body 196 to protect the eyes of wearer 14 from liquid splash or liquid spray propelled at an angle relative to the face of wearer 14.

Lower edge 197 of visor 190 includes a different configuration as compared to lower edge 96 of visor 90. Bonded areas 200 and 202 associated with visor 190 are placed lower on the exterior of mask 212 as compared to bonded areas 100 and 102 associated with visor 90. Also, notch 198 of visor 190 has a keyhole-type configuration defined in part by slot 201 extending upwardly from lower edge 197 and circular portion 203 formed thereon.

An important benefit resulting from the use of flaps 30 and 32 is the ability to attach various types of visors to the associated mask and to vary the location of the corresponding bonded area as required to provide the desired fit between the respective visor and the associated filter body.

In FIG. 7, mask 212 is shown with tie 118 extending from bonded area 122. The use of ties 116 and 118 was previously described with respect to mask 212 as shown in FIGS. 4 and 6. If desired, ties 116 and 118 may be replaced by continuous loop of resilient material 216 as shown in FIG. 8. The use of continuous loop 216 eliminates the need for bonded areas 120 and 122. As previously noted, eliminating the bonded areas associated with flaps 30 and 32 further enhances the fluid barrier formed by the respective flaps and the wearer's face. Also, loop 216 may be placed about the head of wearer 14 as shown in either FIG. 1 or FIG. 9. Flaps 30 and 32 allow the use of loop 216 with masks 12 and 112 in addition to mask 212.

An alternative arrangement for using tie strips 16 and 18 to secure mask 12 with the face of wearer 14 is shown in FIG. 9. As previously noted, the arrangement of surgical tie 16 and 18 is such that portions 16a and 18a extend from top edge 44. Portions 16b and 18b extend from bottom edge 46. For some applications it may be desirable to cross portion 16b over portion 16a (not shown) and portion 18b over portion 18a as shown in FIG. 9. The respective portions 16b and 18b may then be tied with each other over the top of the head of wearer 14. The respective portions 16a and 18a may be tied with each other generally about the back of the head of wearer 14. This configuration of tie strips 16 and 18 results in portions 16b and 18b cooperating with each other to urge bottom edge 46 of face mask 12 into tight engagement below the chin of wearer 14. In the same manner, portions 16a and 18a cooperate with each other to extend in a generally linear continuation from top edge 44 and urge top edge 44 into fluid tight engagement with the face of wearer 14. Also crossing the respective portions 16a and 16b and 18a and 18b results in additional compression of the respective flaps 30 and 32 which further enhances the fluid seal formed between the respective flaps 30 and 32 and the adjacent portion of the face of wearer 14. As demonstrated in FIGS. 1 and 9, flaps 30 and 32 cooperate with tie strips 16 and 18 to provide the optimum pull angle and the optimum amount of force to form the desired fluid barrier between the periphery of mask 12 and the face of wearer 14.

As previously noted, flaps 30 and 32 may have a U-shaped cross-section, a C-fold configuration, or a J-configuration. In addition, flaps 30 and 32 may be formed from a single layer of material with the associated tie strips 116 and 118, or loop 216 threaded through a plurality of small slits (not shown) in each flap 30 and 32. The small slits would allow the associated tie strip to gather and compress the respective flaps similar to a C-fold or U-shaped section.

Although the present invention has been described in detail with respect to alternative embodiments, various changes and modifications may be suggested to one skilled in the art, and it should be understood that various changes, substitutions, and alterations can be made hereto without departing from the spirit and scope of the invention as defined by the appended claims.

What is claimed is:

1. A surgical style face mask comprising:

a non-molded flexible filter body sized to fit over the mouth and nose of a wearer, the filter body having top and bottom edges with the top edge arranged to extend across the nose and cheeks of the wearer and the bottom edge arranged to extend under the chin of the wearer, and said filter body having multiple pleats and a generally rectangular configuration, and an elongated malleable member located in the top edge for conforming the top edge to the contours off the wearer's nose and cheeks;

a flap attached to each side of the filter body and arranged to extend from the filter body;

each flap formed from flexible material that is different from the material used to form the filter body;

means for gathering said flaps into sealing contact with a wearer's face, said means for gathering comprising first securing means and second securing means attached to the respective flaps and arranged to extend generally about the head of the wearer, the first and second securing means extending through the flaps for urging the top edge and the bottom edge into tight engagement with the face of a wearer and for gathering said flexible flap material to prevent undesired fluid flow between the top edge, the bottom edge between the respective sides of the filter body and the face of the wearer.

2. The mask of claim 1 wherein the filter body further comprises an intermediate layer of material which is gas permeable in both directions through the filter body and liquid impermeable in the direction from outside the filter body to inside the filter body.

3. The mask of claim 1 wherein the filter body further comprises an intermediate layer of filter media formed essentially from expanded polytetraflouroethylene (PTFE).

4. The mask of claim 1 further comprising the flaps formed from fluid impervious material with a generally C-fold section attached to the filter body.

5. The mask of claim 1 further comprising the flaps formed from a plastic membrane.

6. The mask of claim 1 further comprising the flaps formed from a closed cell foam material.

7. The mask of claim 1 further comprising the flaps and the associated securing means cooperating with each other such that the flaps are compressed to form an enhanced fluid barrier between the periphery of the mask and the face of a wearer.

8. The mask of claim 1 wherein the first and second securing means consisting essentially of surgical ties formed from resilient material.

9. The mask of claim 1 wherein said filter body further comprises a first layer of bicomponent material disposed on one side of an intermediate layer of expanded polytetrafluoroethylene and a second layer of the same bicomponent material disposed on the opposite side of the layer of expanded polytetrafluoroethylene.

10. The mask of claim 1 further comprising:

each flap formed by folding the flexible material to define a generally U-shaped folded section attached to the respective side of the filter body;

the first securing means extending through the U-shaped folded section of its respective flap; and the second securing means extending through the U-shaped folded section of its respective flap.

11. The mask of claim 10 further comprising:

the first securing means bonded to its respective flap at a location proximate the midpoint of the associated U-shaped folded section; and the second securing means bonded to its respective flap at a location proximate the midpoint of the associated U-shaped folded section.

12. The mask of claim 1 further comprising:

each flap formed by folding the flexible material to define a generally C-fold section attached to the respective side of the filter body;

the first securing means extending into the C-fold section of its respective flap with one end of the first securing means bonded near the bottom of its respective flap; and the second securing means extending into the C-fold section of its respective flap with one end of the second securing means bonded near the bottom of its respective flap.

13. A method for preventing liquids and aerosols from contacting the face of a person wearing a flexible, non-molded surgical style face mask having a plurality of layers of selected materials, comprising the steps of:

placing each layer of material having a generally rectangular shape and a top edge, a bottom edge, and lateral sides in juxtaposition to form a filter body for the mask;

pleating the layers of material;

connecting the layers of material along the top edge, bottom edge and the lateral sides of the generally rectangular shape to form the filter body;

forming a pair of flexible flaps from material that is different from the selected material used to form the filter body;

attaching the flaps to respective sides of the filter body;

providing means for gathering said flaps into sealing contact with a wearer's face, said means for gathering comprising securing means extending through each flap for holding the mask on the face of a wearer for gathering said flexible flap material, and for preventing undesired fluid flow to between the respective sides of the mask body and a wearer's face providing an elongated malleable member in the top edge of the mask body for conforming the top edge to the contours of a wearer's nose and cheeks; and positioning said mask body over the nose and mouth of a wearer such that the bottom edge of the mask body extends under the chin of the wearer, to prevent undesired fluid flow between the top edge, the bottom edge, and a wearer's face.

14. The method of claim 13 further comprising the steps of:

placing an intermediate layer of filter media having a generally rectangular shape in juxtaposition with an inner layer and an outer layer to form the filter body;

folding fluid impervious material to form a generally U-shaped flap for attachment to one side of the filter body; and folding fluid impervious material to form a generally U-shaped flap for attachment to the other side of the filter body.

15. The method of claim 13, wherein the step of attaching the securing means with its respective flap further comprises the steps of:

forming each securing means from a surgical tie strip; and bonding a portion of each tie strip intermediate the ends of the tie strip at a location near the midpoint of the respective flap to allow compressing the respective flap by the surgical tie strip.

16. The method of claim 13 wherein the step of attaching the securing means with its respective flap further comprises the steps of:

forming each securing means from a surgical tie strip; and bonding one end of each surgical tie strip adjacent to the bottom of its respective flap to allow gathering the respective flap by the surgical tie strip.

17. The method of claim 13 further comprising the steps of:

forming the filter body by ultrasonically sealing around the perimeter of the layers of material; and ultrasonically sealing each flap with its respective side of the filter body.

18. The method of claim 13 further comprising the step of compressing the flaps by placing the securing means over the head of the wearer to form a fluid barrier between the periphery of the mask and the face of a wearer.

19. The method of claim 13 further comprising the steps of:

bonding a first securing means to its respective flap at a location proximate the mid point of the respective flap with a first portion of the first securing means extending from the upper part of the respective flap and a second portion of the first securing means extending from the lower portion of the respective flap;

bonding a second securing means to its respective flap at a location proximate the mid point of the respective flap with a first portion of the second securing means extending from the upper part of the respective flap and a second portion of the second securing means extending from the lower portion of the respective flap;

crossing the first portion and the second portion of the respective securing means to compress the respective flaps; and tying the second portion of each securing means over the head of a wearer and tying the first portion of each securing means behind the head of a wearer.

20. A surgical style face mask comprising:

a non-molded flexible filter body having a generally rectangular configuration and multiple pleats sized to fit over the mouth and nose of a wearer, the filter body having top and bottom edges with the top edge arranged to extend across the nose and cheeks of the wearer and the bottom edge arranged to extend under the chin of the wearer;

an elongated malleable member located in the top edge for conforming the top edge to the contours of a wearer's nose and cheeks;

a flap attached to each side of the filter body and arranged to extend from the filter body;

the flaps formed from fluid impervious, resilient material;

means for gatheriing said flaps into sealing contact with a wearer's face, said means for gathering comprising:

first securing means and second securing means attached to respective flaps and arranged to extend generally about the head of the wearer, the first and second securing means extending through the respective flaps for urging the top edge and the bottom edge into tight engagement with the face of the wearer to prevent undesired fluid flow between the top edge and the bottom edge and the wearer's face;

and for gathering the flaps and each respective side of the filter body to prevent undesired fluid flow between the respective sides of the filter body and the face of the wearer.

21. The mask of claim 20 further comprising:

the fluid impervious, resilient material of each flap folded to define a generally C-shaped section attached to the filter body; and each securing means extending through the respective C-shaped section.

22. The mask of claim 20 wherein the first and second securing means comprise surgical ties formed from resilient material and each flap cooperating with its respective securing means to form an enhanced fluid barrier between the periphery of the mask and the face of a wearer.

23. A surgical style face mask comprising:

a non-molded flexible filter body formed from multiple layers of material having a generally rectangular configuration and multiple pleats sized to fit over the mouth and nose of a wearer, the filter body having top and bottom edges with the top edge arranged to extend across the nose and cheeks of the wearer and the bottom edge arranged to extend under the chin of the wearer;

an elongated malleable member located in the top edge for conforming the top edge to the contours of a wearer's nose and cheeks;

a flap attached to each side of the filter body and arranged to extend from the filter body;

each flap formed from flexible material different from that of the mask body;

means for gathering said flaps into sealing contact with a wearer's face, said means for gathering comprising:

a securing means attached to the respective flaps and arranged to extend generally about the head of the wearer, the securing means extending through the flaps for urging the top edge and the bottom edge into tight engagement with a wearer's face to prevent undesired fluid flow between the top edge and the bottom edge and a wearer's face and gathering each flap to prevent undesired fluid flow between the respective sides of the filter body and the face of a wearer.

24. The mask of claim 23 wherein the securing means further comprises a continuous loop.

25. The mask of claim 23 wherein the securing means further comprises a continuous loop formed from resilient material.

26. The mask of claim 23 wherein the filter body further comprises at least one pleat to minimize collapsing of the face mask against the face of a wearer and to provide benefits of an off-the-face style mask.

27. The mask of claim 1 wherein the filter body further comprises multiple pleats which allow expansion of the filter body and at least one of the pleats folded in a reverse direction as compared to the other least to provide the benefits of an off-the-face style mask.

* * * * *

UNITED STATES PATENT AND TRADEMARK OFFICE
CERTIFICATE OF CORRECTION

PATENT NO. : 5,553,608
DATED : September 10, 1996
INVENTOR(S) : Reese, et al.

It is certified that error appears in the above-identified patent and that said Letters Patent is hereby corrected as shown below:

Column 5, line 2, after "trademark", delete "KTON®", and insert -- KRATON® --;

Column 5, line 51, after "chamber", delete "foiled", and insert -- formed --.

Column 6, line 16, after "preferable", delete "o" and insert -- to --;

Column 6, line 20, after "least", delete "on", and insert -- one --;

Column 7, line 2, after "16", delete "an", and insert -- and --;

Column 7, line 15 after "contact", insert -- with --.

Column 12, line 25, after "contours", delete "off", and insert -- of --.

Signed and Sealed this

Sixteenth Day of September, 1997

*Attest:*

BRUCE LEHMAN

*Attesting Officer*  Commissioner of Patents and Trademarks